United States Patent [19]
Tachibana et al.

[11] Patent Number: 5,401,237
[45] Date of Patent: Mar. 28, 1995

[54] BLOOD PROCESSING FOR TREATING BLOOD DISEASE

[75] Inventors: Shunro Tachibana, Fukuoka; Ichiro Sogawa, Osaka; Katsuro Tachibana, Fukuoka, all of Japan

[73] Assignee: Shunro Tachibana, Fukuoka, Japan

[21] Appl. No.: 905,245

[22] Filed: Jun. 26, 1992

[30] Foreign Application Priority Data

Jun. 28, 1991 [JP] Japan .................. 3-158775

[51] Int. Cl.⁶ .............................. A61M 37/00
[52] U.S. Cl. ...................... 604/4; 128/660.03
[58] Field of Search ............ 604/4, 5, 6, 19; 128/660.03; 204/157.62

[56] References Cited

U.S. PATENT DOCUMENTS

| | | | |
|---|---|---|---|
| 4,381,004 | 4/1983 | Babb. | |
| 4,787,883 | 11/1988 | Kroyer | 604/4 |
| 4,820,260 | 4/1989 | Hayden | 604/4 |
| 4,855,064 | 8/1989 | Schlein | 604/4 X |
| 4,971,991 | 11/1990 | Umemura et al. | 204/157.62 X |
| 5,150,705 | 9/1992 | Stinson | 604/4 X |
| 5,158,071 | 10/1992 | Umemura et al. | 128/660.03 X |

FOREIGN PATENT DOCUMENTS 0108658 5/1989 European Pat. Off.
91/03264 3/1991 WIPO.

OTHER PUBLICATIONS

"Science" Japan Edition, Oct. 1988, pp. 65-73 Photophoresis apparatus in treatment of a cutis T cell lymphadenoma.

*Primary Examiner*—Sam Rimell
*Attorney, Agent, or Firm*—W. G. Fasse; W. F. Fasse

[57] ABSTRACT

A method and an apparatus for an effective chemical treatment of a blood disease apply a drug of a wider range with a smaller dose or lower concentration to the blood outside the patient's body. Blood which is collected from a patient is fed through a tube (2a) into a chamber (4) by a pump (3). A drug is injected into the chamber (4) from a container (5), while ultrasonic waves are applied to the blood contained in the chamber (4) from an actuator (7). The blood treated with the drug and by the ultrasonic waves, is returned into the body of the patient through a tube (2c), while the same is monitored by sensors (10) and (11).

24 Claims, 2 Drawing Sheets

FIG. 1           PRIOR ART

BLOOD PROCESSING FOR TREATING BLOOD DISEASE

FIELD OF THE INVENTION

The present invention relates to blood processing, and more particularly, it relates to a blood processing method and a blood processing apparatus for chemically treating a blood disease such as leukemia, and a method of treating the blood disease.

BACKGROUND INFORMATION

In order to chemically treat a blood disease such as leukemia, conventionally a remedy is directly administered into the body of the patient. For example, a patient who receives chemical treatment often gets an intravenous injection of a carcinostatic substance. When he suffers from leukemia, he receives a toxic drug for attacking rapidly propagating leukocytic cells, or such a drug is administered as a relatively high intravascular concentration for attaining a good effect. The above procedures often lead to various side reactions.

On the other hand, there has been developed a new chemical treatment method employing an apparatus called a photophoresis apparatus for treating of a cutis T cell lymphadenoma (CTCL) ("Science" Japan Edition, October 1988, pp. 65–73). As shown in present FIG. 1, such a photophoresis apparatus 20 comprises a centrifugal separator 21 for separating blood into its components, and is controlled by a microprocessor. In the known apparatus, blood components contained in a bag 22a are fed through a transparent passage 23 of plastic, to be stored in another bag 22b. High-power ultraviolet lamps 24 are provided on both sides of the passage 23 meandering through a space between the lamps 24. The blood of a patient is separated into components by the centrifugal separator 21, so that blood plasma and leukocytes are contained in the bag 22a. The components thus contained in the bag 22a are mixed with a physiological salt solution which is contained in a bag 22c and fed into the passage 23. The ultraviolet lamps 24 apply intense ultraviolet radiation (UVA) to the liquid which is passed through the passage 23. The UV-irradiated components are mixed with other centrifugally separated components, and returned into the body of the patient.

The above photophoresis apparatus provides a device for optically processing the blood or the blood components of a patient with a drug outside of the patient's body. Such a device may provide a way for chemically treating and optically activating a drug and selectively applying the drug to a target in a patient's blood.

SUMMARY OF THE INVENTION

The inventors have found that it is necessary to study not only the optical activation of a drug but also the improvement of the drug action in a wider range. When a drug is optically activated, it may be necessary to take the light transmittance of an object such as blood into consideration in order to attain a sufficient activation, and hence the treatment conditions may be restricted. Particularly in the treatment of a blood disease, there is a need for a method or device that will provide an effective treatment even if various drugs to be administered are applied in a low concentration.

In order to satisfy such need, it is an object of the present invention to provide a method and an apparatus for an effective treatment by applying a wider range of a drug with a smaller dose or lower concentration, particularly for the chemical treatment of a blood disease.

According to a first aspect of the present invention, there is provided a blood processing apparatus which comprises a passage having an inlet and an outlet for passing blood therethrough, a pump for feeding the blood from the inlet toward the outlet of the passage, a drug injection device for injecting a drug into the passage, and an ultrasonic wave application device for applying ultrasonic waves to the blood which is mixed with the drug in the passage.

In the blood processing apparatus according to the present invention, the blood of a patient is supplied into the passage from the inlet, so that the blood can be fed toward the outlet by the pump. In the passage, the blood is mixed with a drug by the drug injection device. The ultrasonic wave application device applies ultrasonic waves to the blood which is mixed with the drug. Thus, the blood of the patient is ultrasonic-treated with the drug, and then discharged from the outlet of the passage.

According to the method of the present invention, the blood of a patient is fed through a tubular structure, for example, at a prescribed flow rate. An effective dose of a drug is added to the blood in this tubular structure, whereby the drug can be maintained in constant concentration in the blood. Simultaneously with or following such addition of the drug, ultrasonic waves are applied to the blood. The blood treated by the ultrasonic waves is discharged from the structure and introduced into the body of the patient.

According to the present invention, the ultrasonic-treated blood is preferably regularly monitored. Various sensors can be employed for this purpose.

After the ultrasonic treatment, the drug which is left in the blood is preferably removed in order to suppress a side reaction caused on the patient. In this case, the blood is supplied to the patient after such removal of the drug.

According to another embodiment of the present invention, blood is first collected from a patient. Then, an effective dose of a drug is added to the blood. Simultaneously with or following such addition of the drug, ultrasonic waves are applied to the blood. The ultrasonic-treated blood is returned into the body of the patient.

This treatment method can be applied to leukemia, for example. In this case, a carcinostatic substance, for example, is added to the collected blood, in order to attack malignant lymphocytic cells.

This treatment method can be carried out while the blood of the patient is circulated by an external circulation system outside of the patient's body. In this case, the drug is continuously or intermittently added to the externally circulating blood. The blood containing the drug is treated with ultrasonic waves.

Also in this treatment method, the ultrasonic-treated blood is preferably monitored. Further, the drug which is added to the blood is preferably removed before the blood is returned into the body of the patient.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
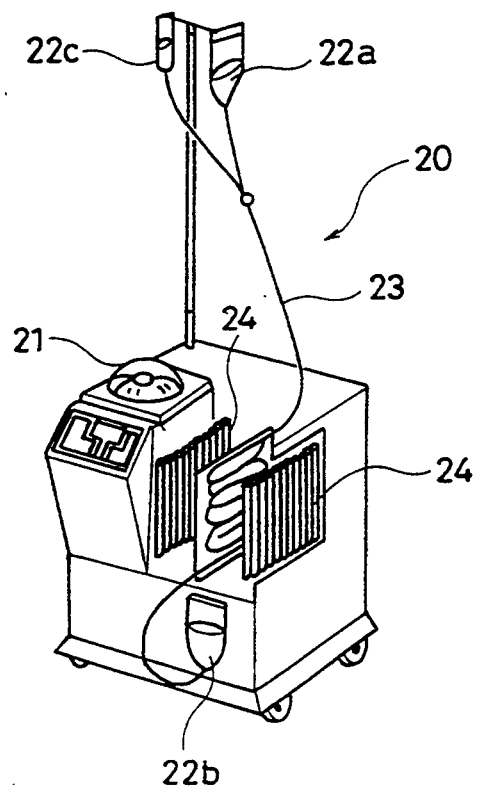
FIG. 1 is a perspective view showing a conventional blood processing apparatus.
Figure 2:
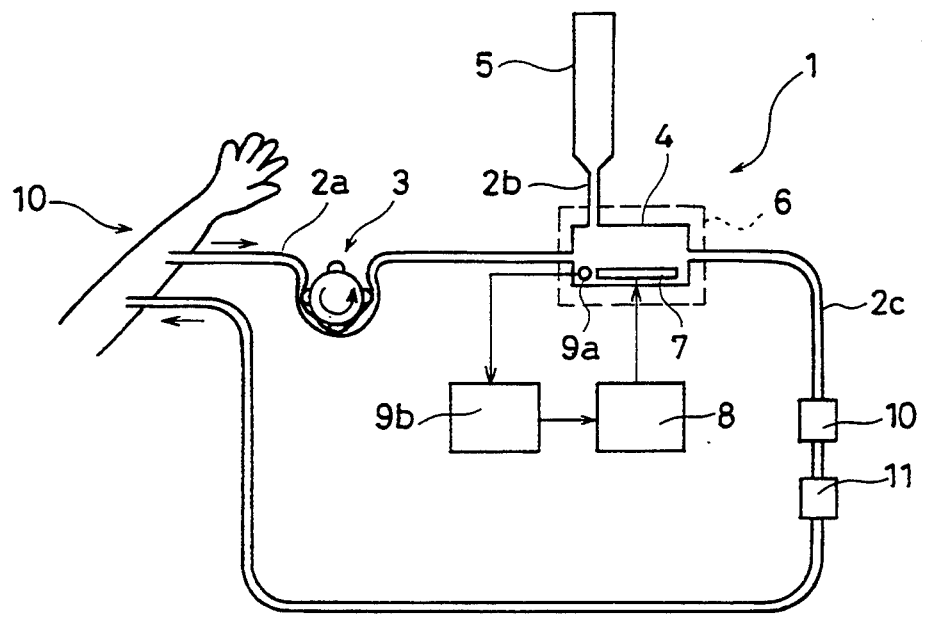
FIG. 2 is a typical diagram showing a concrete example of a blood processing apparatus according to the present invention.

FIG. 2 is a typical diagram showing an example of an apparatus 1 for processing blood according to the present invention. In this blood processing apparatus 1, a tube 2a for introducing the blood of a patient P into the apparatus 1 is connected to a chamber 4. The tube 2a, which is made of vinyl chloride resin, polyethylene, silicone resin or the like, for example, is wound on a rotary head of a separate roller pump 3. Thus, the introduced blood is fed to the chamber 4 at a constant flow rate. On the other hand, the chamber 4, which is adapted to mix the blood with a drug and treat the same with ultrasonic waves, is provided with a container 5 for the drug and for feeding the drug through a tube 2b. The drug is introduced into the chamber 4 at a constant flow rate by a separately provided pump, not shown. The chamber 4 can be kept warm by a heater 6 which is provided on its outer periphery. The chamber 4 is provided with an ultrasonic actuator 7, which is connected with a transmission circuit 8 provided outside the chamber 4. The ultrasonic actuator 7, which is capable of generating ultrasonic waves in a frequency range of 10 KHz to 10 MHz, for example, can be formed by an electrostrictive element or a magneto-strictive element. The chamber 4 is further provided with an ultrasonic power monitor or sensor 9a for controlling the ultrasonic waves. The sensor 9a is electrically connected with an ultrasonic power monitor circuit 9b provided outside of the chamber 4. The transmission circuit 8 is controlled by a signal which is detected by the sensor 9a and processed by the monitor circuit 9b, thereby controlling the ultrasonic wave output. A tube 2c is provided in the chamber 4 in a portion opposite to the tube 2a, in order to discharge the fluid from the chamber 4. The tube 2c, which can be made of vinyl chloride resin, polyethylene or silicone resin similarly to the tube 2a, can be provided with a hemolysis sensor 10 and a bubble sensor 11. The hemolysis sensor 10 is made of a member for detecting hemolysis by change of light transmittance, or the like. The state of the blood discharged from the tube 2c can be monitored by the sensors 10 and 11. If necessary, still another sensor may also be provided. The tube 2c can be used for returning the blood into the body of the patient P. In the apparatus 1 having the aforementioned structure, the blood of the patient P is mixed with a proper dose of a drug and treated with ultrasonic waves in the chamber 4, and thereafter returned into the body of the patient P. Thus, the apparatus 1 shown in FIG. 2 can be employed as an external circulation system, while the same can also be used as an apparatus for processing separately collected blood.

Figure 3:
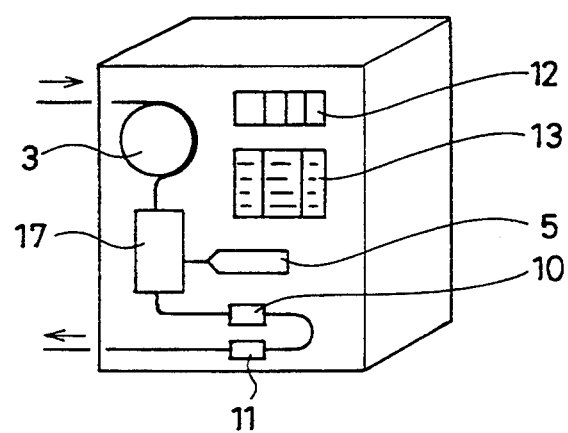
FIG. 3 is a perspective view showing an assembled state of the apparatus shown in FIG. 2.

The apparatus 1 typically illustrated in the aforementioned mannner can be assembled as shown in FIG. 3, for example. In the apparatus shown in FIG. 3, a display 12 displays feed rates of the pump 3 and another pump, not shown, for supplying the drug into the container 5, the output of an ultrasonic unit 17, the temperature of the chamber 4, and data from the hemolysis sensor 10 and the bubble sensor 11. The feed rates, the output of the ultrasonic unit 17, the temperature of the chamber 4 and the like can be controlled by an operation panel 13. In relation to this apparatus, it is possible to provide another system for supplying another drug, thereby supplying a plurality of drugs into the chamber 4. Further, when the tube 2c for discharging the blood which has been processed in the chamber 4, is provided with other treatment elements, such as a filter, for example, for removing the drug, it is possible to remove only the drug from the blood, thereby effectively suppressing a side reaction. In addition, portions of the apparatus for passing the blood therethrough, such as the tubes 2a to 2c and the chamber 4, for example, can be formed by throw-away members. Further, outlets for taking the blood before and after processing can be formed on the tubes 2a and 2c connected to the chamber 4.

According to the present apparatus, as hereinabove described, the ultrasonic waves act on the blood components to improve the sensitivity of these blood components to the drug. When the blood of a leukemic patient is processed, for example, the ultrasonic waves act on malignant lymphocytic cells to improve the sensitivity to a carcinostatic substance. Consequently, it is possible to attain a preferable chemical treatment effect with a smaller dose of a drug. Since the drug is locally administered into the blood within the chamber, it is possible to attack the target with no waste. When the blood is returned into the body of the patient, the drug, which had an effective concentration within the chamber 4, is so diluted that its toxicity is reduced. When the drug is removed from the blood by some device, e.g. a filter described above, it is possible to maintain an intravascular concentration of the drug at a lower value all over the body of the patient. Thus, it is possible to remarkably reduce side reactions caused by the drug.

As hereinabove described, the present invention is adapted to mix blood with a drug and treat the same with ultrasonic waves, thereby improving the effect of the drug, particularly that for a blood disease, over a very wide range. According to the present invention, it is possible to achieve a synergistic chemical treatment effect by the ultrasonic waves and the drug. According to the present invention, further, it is possible to effectively apply the drug with a small dose or small intravascular concentration, thereby reducing a side reaction. Thus, the present invention is very effectively applied to the chemical treatment of a blood disease such as leukemia, autoimmune disease such as AIDS, sepsis and collagen disease, in particular.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for processing blood, comprising a passage having an inlet and an outlet for passing blood therethrough; a pump for feeding said blood from said inlet toward said outlet in said passage; drug injection means for injecting a drug into said passage; and ultrasonic wave application means for improving an effectiveness of said drug on a component of said blood by applying ultrasonic waves to said blood mixed with said drug in said passage.

2. The apparatus in accordance with claim 1, further comprising a treatment sensor for monitoring relevant blood characteristics of said blood discharged from said passage.

3. The apparatus in accordance with claim 1, further comprising removal means for removing said drug from said blood flowing in said passage after injection of said drug.

4. The apparatus in accordance with claim 1, wherein said passage comprises a tube for introducing said blood, and a chamber connected with said tube for mixing said blood with said drug while applying ultrasonic waves therein.

5. The apparatus in accordance with claim 4, wherein said ultrasonic wave application means comprise an ultrasonic transmission element provided in said chamber, an ultrasonic transmission control circuit outside said chamber, and means connecting said ultrasonic transmission element to said ultrasonic transmission control circuit outside said chamber.

6. The apparatus in accordance with claim 1, as applied to an external circulation system for treating a patient.

7. A method for processing blood, comprising:
(a) feeding blood into a treatment passage at a treatment rate;
(b) adding a quantity of a drug to said blood in said passage;
(c) applying ultrasonic waves to said blood containing said drug in said treatment passage, for improving an effectiveness of said drug on a component of said blood; and
(d) discharging ultrasonic-treated blood from said passage.

8. The method in accordance with claim 7, further comprising monitoring treatment relevant characteristics of said blood discharged from said treatment passage.

9. The method in accordance with claim 7, further comprising removing said drug left in said blood before discharge of said blood from said treatment passage.

10. The method of claim 7, wherein said blood is whole blood and said blood is not separated during any step of said method, wherein said ultrasonic waves are applied to said whole blood.

11. The method of claim 7, wherein said blood is not heated above normal body temperatures during said method.

12. The method of claim 7, wherein said blood component is a component other than red cells.

13. The method of claim 12, wherein said blood component is lymphocytic cells.

14. A method of treating a patient having a blood disease, said method comprising:
(a) collecting blood from said patient;
(b) adding a drug to said collected blood;
(c) applying ultrasonic waves to said blood containing said drug for improving an effectiveness of said drug on a component of said blood; and
(d) returning ultrasonic-treated blood into the body of said patient.

15. The method in accordance with claim 14, further comprising correlating a definite volume of said blood continuously collected from said patient to a prescription dose of said drug and to a prescription dose of said ultrasonic waves, and then continuously returning treated blood into the body of said patient.

16. The method in accordance with claim 14, further comprising removing said drug still left in said blood after said application of ultrasonic waves and before said blood is returned into the body of said patient.

17. The method in accordance with claim 14, further comprising monitoring said ultrasonic-treated blood for treatment relevant characteristics.

18. The method in accordance with claim 14, wherein a disease of said blood is leukemia.

19. The method in accordance with claim 14, wherein said drug includes a carcinostatic substance.

20. The method in accordance with claim 18, wherein said drug includes a carcinostatic substance.

21. The method of claim 14, wherein said blood is whole blood and said blood is not separated during any step of said method, wherein said ultrasonic waves are applied to said whole blood.

22. The method of claim 14, wherein said blood is not heated above normal body temperatures during said method.

23. The method of claim 14, wherein said blood component is a component other than red cells.

24. The method of claim 23, wherein said blood component is lymphocytic cells.

* * * * *